United States Patent [19]

Klaue et al.

[11] Patent Number: 5,376,123
[45] Date of Patent: Dec. 27, 1994

[54] ADAPTABLE STEM FOR ENDOPROSTHESIS

[75] Inventors: Kaj Klaue, Spiegel, Switzerland; Jean L. Chareire, Levallois, France

[73] Assignee: AO-Forschungsinstitut Davos, Davos, Switzerland

[21] Appl. No.: 54,832

[22] Filed: Apr. 30, 1993

Related U.S. Application Data

[63] Continuation of Ser. No. 741,452, Aug. 7, 1991, filed as PCT/CH90/00281, Dec. 5, 1990, abandoned.

[51] Int. Cl.$^5$ .................. A61F 2/36; A61F 2/32
[52] U.S. Cl. ..................... 623/23; 623/16; 623/18
[58] Field of Search .............. 623/16, 17, 18, 19, 623/20, 22, 23

[56] References Cited

U.S. PATENT DOCUMENTS

| 4,650,489 | 3/1987 | Thompson | 623/16 |
| 4,778,474 | 10/1988 | Homsy | 623/16 |
| 4,851,004 | 7/1989 | Homsy | 623/16 |
| 4,904,258 | 2/1990 | Pommier et al. | 623/16 |
| 4,944,754 | 7/1990 | Linkow et al. | 623/16 |
| 4,963,151 | 10/1990 | Ducheyne | 623/16 |
| 5,035,713 | 7/1991 | Friis | 623/16 |
| 5,133,767 | 7/1992 | Frey et al. | 623/16 |

Primary Examiner—David Isabella
Assistant Examiner—Debra S. Brittingham
Attorney, Agent, or Firm—Walter C. Farley

[57] ABSTRACT

A stem for an endoprosthesis to be anchored in a bone (3) comprises a chamber (4) which surrounds the stem periprosthetically, which can be sealed in a pressure tight manner and which can be expanded with a thermoplastic or thermostable filling material (16). The rigid stem (1) of the endoprosthesis is connected mechanically to the bone (3) via the expandable chamber (4) by means of the filling material (16). The filling material is isolated from the bone (3), however, by the wall of the pressure-tight chamber (4). This makes it possible to ensure that the outer wall of the chamber (4) adjacent to the bone is extremely biocompatible.

21 Claims, 7 Drawing Sheets

ADAPTABLE STEM FOR ENDOPROSTHESIS

This is a continuation of U.S. application Ser. No. 07/741,452, filed Aug. 7, 1991, filed as PCT/CH90/00281, Dec. 5, 1990, now abandoned.

This invention relates to a stem for an endoprosthesis to be anchored in a bone, and its anchoring into joint endoprostheses, in particular hip prostheses.

Stem prostheses of this kind as a rule evince a rigid, shank-like metal or composite segment affixed with or without bone cement into a prepared bone cavity of the femur.

As to the so-called cemented prostheses, the cement closes off the inside surface of the tubular bone. The drawbacks of this known implant technique are, on one hand, the exothermal reaction of the polymerizing cement and, on the other hand, the cement filling all medullary cavities irrespective of the hardness of their walls; as a result, the bonding, at least as regards mechanical strength, takes place between prosthesis and bone by means of a highly heterogeneous surface layer. If there are not enough hard bone zones in this interface, loosening can rapidly occur. It is known that micro-displacements arise very rapidly (months to years) between the prosthesis and the bones, long before becoming clinically relevant. However micro-displacements cause progressive bone resorption which subsequently becomes clinically and radiologically obvious. Optimally the cement is biologically inert without biological affinity for the bone cells. Therefore there always shall be a so-called foreign-body membrane which, at least on the prosthesis side, will not hold.

As to the so-called cement-free prostheses, the attempt is made to clamp them and thus to achieve incorporation and fixation free from displacement. It is clear per se that the inherent lack of congruence between the prosthesis and the bone entails point contact sites with local overstress. If these local sites are cyclically overstressed— a highly probable eventuality under functional conditions—medullary bone resorption and periosteous apposition may result, as shown in animal experimentation, so that, ultimately, loosening again takes place. On the other hand there are advantages, namely the eliminated overheating and better bone affinity made possible by a variety of materials (titanium plasma, hydroxy-apatite, carbon), and lastly the improvement of extraction feasibility of the prosthesis.

The European patent document A1 0,323,800 (Mecron) furthermore discloses an implantable prosthesis stem with a biologically compatible, elastic, membrane-like plastic sleeve. Because this known sleeve has a defined wall thickness, no really satisfactory matching to the bone cavity can be achieved by it. Moreover the sleeve's biological compatibility much of the time cannot be fully exploited because bone cement must be still used to achieve reliable anchoring.

Lastly, the European patent document A1 0,328,848 (Sulzer) discloses a reticular reinforcement not connected to the prosthesis stem, that is, to be implanted separately. This reinforcement is cup-shaped and in the form of several layers and serves as a boundary layer between the bone cement and the marrow cavity. Because this known reinforcement is an open system, i.e., it is not pressure-tight, the bone cement injected as a filler between the prosthesis stem and the reinforcement can exert only slight pressure on the individual layers of the reinforcement, so that, again, matching the reinforcement shape to the irregular marrow cavity is quite limited. However the special drawback is the passage of the bone cement through the individual layers of the reinforcement into the marrow cavity, both proximally and out of the cavity, as a result of which undesired contact between the bone cement and human tissue again takes place.

The object of the invention is palliation. The object of the invention is to create a stem for an endoprosthesis to be anchored into a tubular bone and combining the advantages of both cemented and uncemented prostheses while overcoming the cited drawbacks in that the "mobile", biologically active, transforming bone wall always remains in biologically affinitive contact with the dynamically expanding stem because of this stem's continuous, morphological adaptability.

The invention achieves this goal by a stem evincing the features of claim 1 and by using a stem with the features of claim 23.

Essentially the invention's advantages are that, because of the stem of the invention, separate solutions are made possible for the problems of biological affinity and mechanical adhesion.

The rigid endoprosthesis stem is mechanically connected by a filler material with the bone. In addition, this filler material is separated from the bone by the wall of an impermeable chamber. As a result, a wide range of possibilities always is present to make the outside (bone side) of this chamber as biologically compatible (biologically affinitive) as possible.

In its empty state, that is when the chamber tightly against the stem is unfilled, the prosthesis stem of the invention is easily introduced into the oversize bone marrow cavity. Then, filling material is expanded in the chamber in order to achieve as good a chamber-bone contact as possible. The hydrostatic pressure forming in the chamber being uniformly distributed, the compression of the inside bone wall also is homogeneous. Where applicable, this pressure also may be constantly monitored using a locally mounted manometer. In order to withstand any pressure that may form at the exposed sites (collar and tip of the prosthesis stem), the chamber walls may be made especially traction-resistant at those sites.

On the other hand, the radial rigidity of the chamber should be slight in order to favor expansion. Suitable materials for the chamber are the following: for low injection-molding pressures, silicone or polyurethane (this material is used in particular in cardiac prosthesis where it has been formal to be highly biologically compatible and thrombosis-inhibiting); for high injection-molding pressures, a textile wall impregnated with the same elastomers.

Advantageously the textile wall evinces the following properties:

It is a braid of two mutually crossing fiber series,

The fibers subtend about 45° with the bone axis to favor radial extension,

The biologically compatible fibers evince high strength, for instance being carbon fibers, polyester or polyamides, or in the event of less biologically compatible fibers, they must be very well sheathed.

In order to keep small the stress on the chamber when it is being filled, its cross-sectional perimeter may be larger than that of the prosthesis stem. The wall thickness shall be less than 0.5 mm, preferably less than 0.25 mm.

Preferably the chamber wall of the stem of the invention is coated with a biologically affinitive material such as hydroxy-apatite. Such a membrane-like chamber is made as follows:

Bonding hydroxy-apatite or carbon powder using a biologically compatible adhesive or incrustation following heating the membrane and pressing the powder, Bonding a textile wall (see above), Using a carbon "velvet" wall in which the base plate of the velvet hairs is impregnated with said elastomers. The reason for the velvet design is the increased contact area with the bone. Bone-velvet offers enormous tensile strength even if the total cross-section of the velvet hairs amounts to no more than 5 to 10% of the total area.

The injected filler may be among the following materials:

(A) HEAT-RESISTANT FILLERS

Illustratively, heat-resistant fillers are 2-component materials that, following polymerization and when subjected to heating, no longer will deform.

When using a heat-resistant material, the following advantages are obtained relative to the conventional cemented prosthesis:

Reduced heat necrosis of the bone due to the thermally insulating membrane.

Freely selected material viscosity (the material may be liquid).

(B) THERMOPLASTIC FILLERS

These are rigid material which upon heating become deformable.

When a thermoplastic is used, the dynamics of bone transformation can be compensated by continuous matching of the prosthetic material.

Mechanically-dynamically, the thermoplastic behaves like a solid, rigid material fully transmitting the functional forces. However a thermoplastic under slight hydroplastic pressure will flow quasi-statically and transmit said pressure integrally and homogeneously to the bone contact areas. As a result, a maximum application area (interface) of prosthesis-bone at minimum unit pressure is achieved.

The prosthesis can be implanted conically into the stem, the loading by gravity and muscle tension causing constant wedging (penetration by prosthesis). In this case and on account of the bone transformation, a "rigid" prosthesis inevitably tends toward loosening.

In this case the thermoplastic adapts to the medullary area of the transforming bone and thereby is able to prevent micro-displacements. It requires, in order to follow the dynamics of this biological process, and to prevent loosening, homogeneous force spreading over a large surface, said spreading if called for being supported by adding more thermoplastic. For this purpose a reservoir with pressurized thermoplastic may be used, this reservoir communicating with the chamber. Accordingly the thermoplastic should meet the following criteria:

1. Its viscosity must be low enough so that:
   (a) problem-free and rapid injection is possible in the absence of:
   excessive temperature,
   excessive pressure,
   (b) adapting its shape at room temperature shall be feasible.

2. At body temperature its viscosity must be high enough to afford reliable bonding as if it were a rigid material and to absorb all dynamic forces.

3. It should evince good biological compatibility (for instance in the event of membrane injury).

In order to achieve the desired viscosity, a solid, biologically compatible powder, also fibers, for instance of carbon, may be admixed with a thermoplastic of rather low viscosity, whereby the viscosity is raised. A similar result may be accomplished using a thermoplastic of which the solid-liquid phase change is too steep at 37° C. Paraffin and stearin are practical examples of thermoplastics of which the viscosity may obey the above criteria. Non-elastomeric silicones also evince good biological compatibility. In the presence of water, silicones change from viscous bodies into elastomers. This property may be useful when they serve as thermoplastic prosthetic fillers in the event a leak occurs in the periprosthetic chamber: as soon as the silicone leaves the chamber, it "coagulates" in contact with the physiological liquid and as an elastomer forms an "automatic" sealant for that leak.

If a heat-resistant cement is used as filler, the dimensions of the periprosthetic chamber will not be limited. If on the other hand a thermoplastic filler is used, then the rigid stem of the endoprosthesis shall "float" in a (slowly) flowing medium. If the acting resulting forces are cumulative in a preferred direction, the prosthesis will slowly trend toward the solid contact between prosthesis and bone.

A variety of illustrative embodiments which at the same time elucidate the functional principle are shown in the drawings and are discussed below.

Figures 1, 1A:
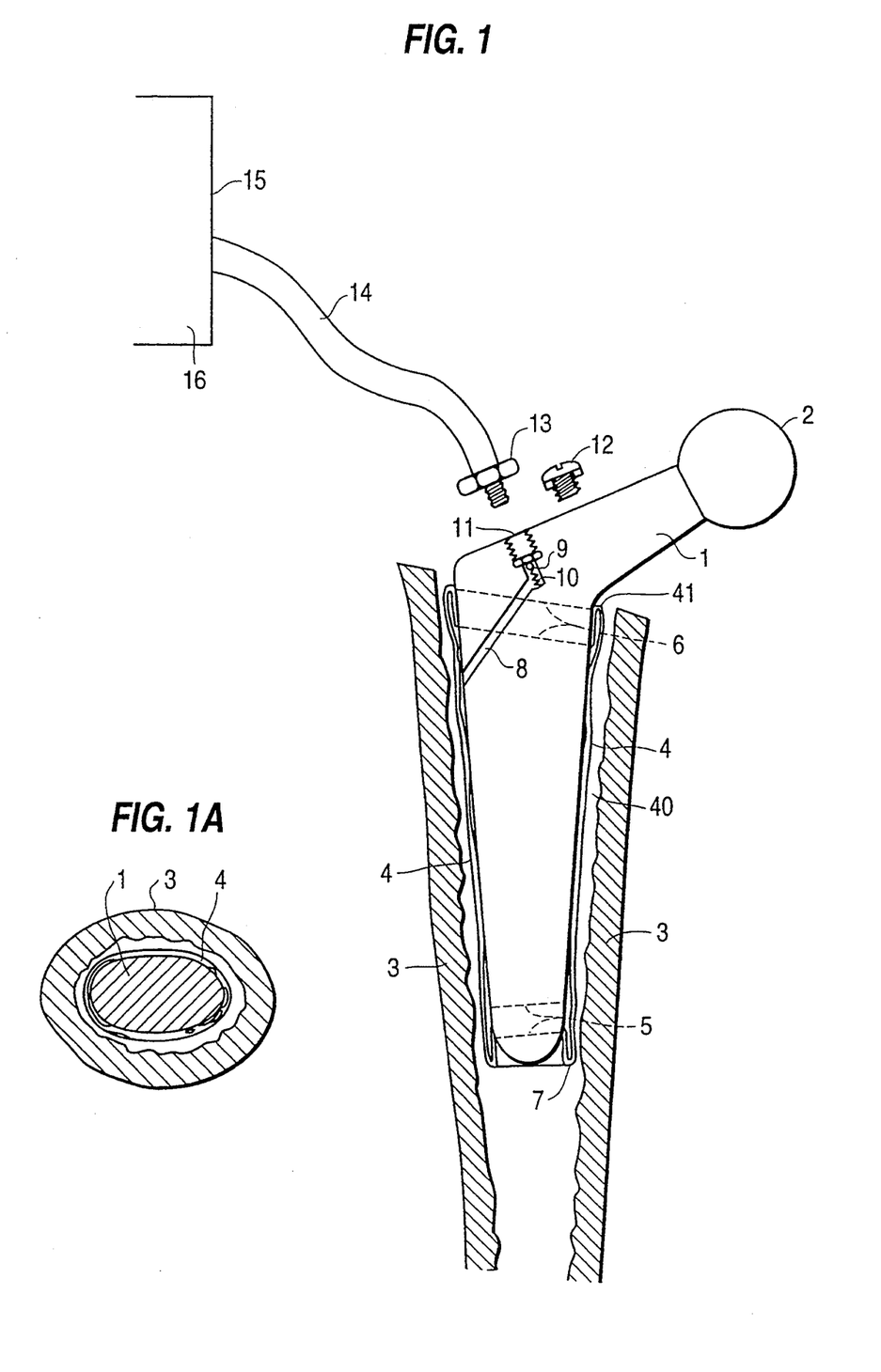
FIG. 1 is a longitudinal section of a hip endoprosthesis stem of the invention with a periprosthetically mounted, empty single chamber immediately upon introduction into the bone marrow cavity.
FIG. 1A is a cross-section at the center of the stem of FIG. 1.

In the preferred embodiment of the invention shown in FIGS. 1 and 1A, a rigid prosthesis stem 1 with a joint head 2 is completely enclosed periprosthetically by an empty chamber 4. The chamber 4 comprises a flexible textile made of silicone or polyurethane and bonded in a pressure-tight manner along a distal affixing zone 5 and a proximal affixing zone 6 to the prosthesis stem 1. A one-way valve 9 with a spring 10 is present at the shoulder region of the prosthesis stem 1 and communicates through a duct 8 with the chamber 4. The valve 9 can be closed in a pressure-tight manner by means of a threaded hole 11 and a tube stub 12. The cavity 40 shown in FIG. 1 between the outer wall of the chamber 4 and the bone 3 which is formed upon insertion of the prosthesis stem 1 with empty chamber 4 into the bone marrow cavity 3 is sealed by the expansion of chamber 4. Following removal of the tube stub 12 and upon threading the filler stub 13 into the threaded hole 11, filler 16 is pumped from the filler reservoir 15 through the filling hose 14, valve 9 and tube 8 into the chamber 4 which thereby widens radially and accordingly, as shown in FIGS. 2 and 2A, complete contact is established between the bone 3 and the outer wall of the chamber 4.

The fluid or viscous filler 16 also may be injected using a syringe which should generate a pressure of about 10 bars. The injection pressure depends on the filler viscosity.

Figure 2:
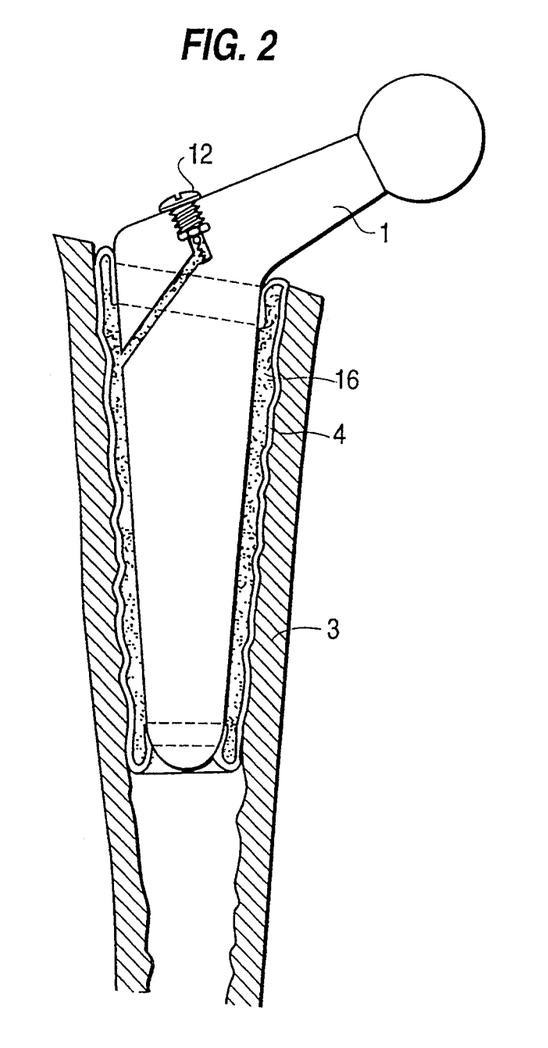
FIG. 2 is a longitudinal section of a hip endoprosthesis stem of FIG. 1 with a filled chamber.
Figure 2A:
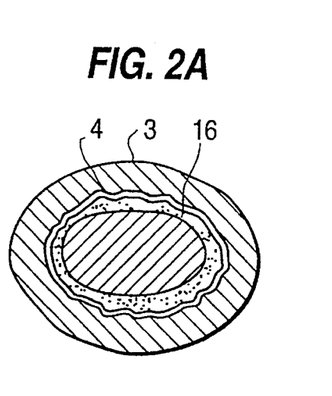
FIG. 2A is a cross-section at the center of the stem of FIG. 2.

In the embodiment of FIGS. 1 and 2, both thermoplastic and heat-resistant fillers may be used.

The textile wall of chamber 4 is bonded to the prosthesis stem 1 in the distal and proximal affixing zones 5 and 6 in such manner that this stem, even when definitively implanted, remains somewhat displaceable axially without losing thereby the achieved complete contact between the chamber 4 and the bone 3. This property of chamber 4, which also is called the "roller conveyor" effect, assumes some significance because frequently sinking or setting of the prosthesis stem into the bone marrow cavity is observed following surgery. The roller-conveyor effect can be achieved by providing a circular fold 7 and 41 in each of the distal and proximal zones in the wall of the chamber 4 as shown in FIGS. 1 and 2.

Figure 3:
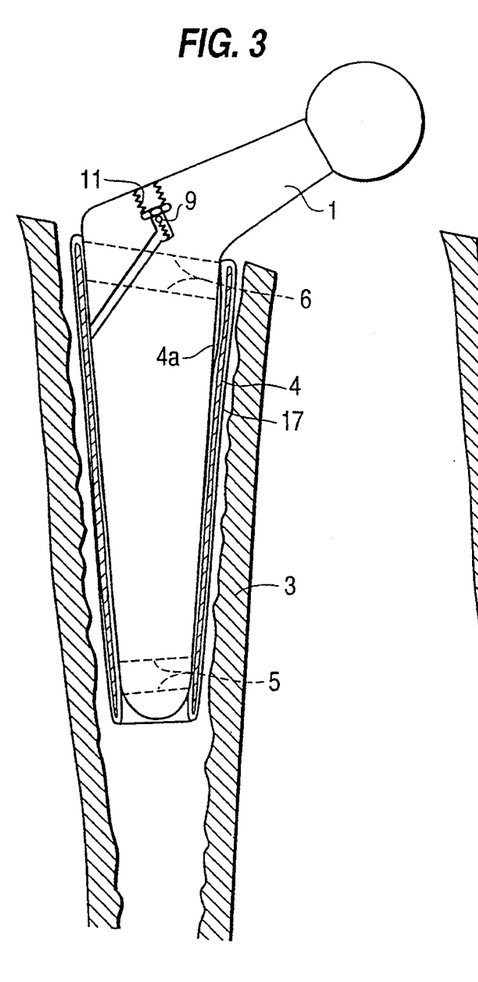
FIG. 3 is a longitudinal section of a stem of the invention when empty, with a chamber near the stem and a chamber near the bone.
Figure 4:
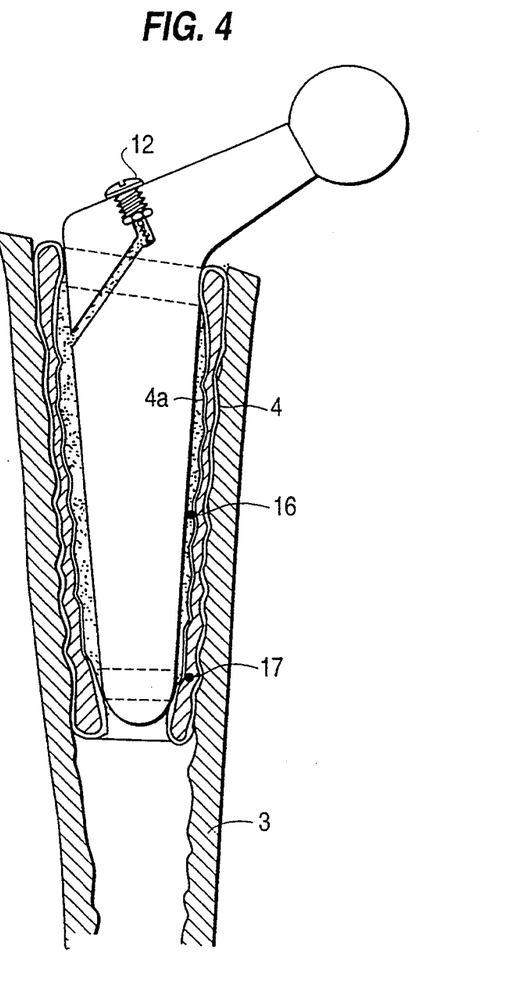
FIG. 4 is a longitudinal section of a hip endoprosthesis of FIG. 3 with a filled chamber.

FIGS. 3 and 4 show another preferred embodiment of the stem of the invention comprising a prosthesis stem 1 with a dual chamber consisting of an outer chamber 4 near the bone and an inner chamber 4A near the prosthesis.

This prosthesis shaft 1 with dual chambers is implanted such that it is inserted into the bone marrow cavity when in its empty condition, namely when the chambers 4 and 4A are empty (FIG. 3). Thereafter, the inner chamber 4A near the prosthesis is filled in situ by injecting a filler 16 through valve 9. Next, the outer chamber 4 near the bone is pressurized with a thermoplastic 17 following light heating, and, if called for, also following replenishing (FIG. 4). Thereby the outer chamber 4 is narrowed down to a fraction of a millimeter.

In the event the prosthesis must be replaced, it can be removed merely by heating the thermoplastic in a suitable manner.

Figure 5:
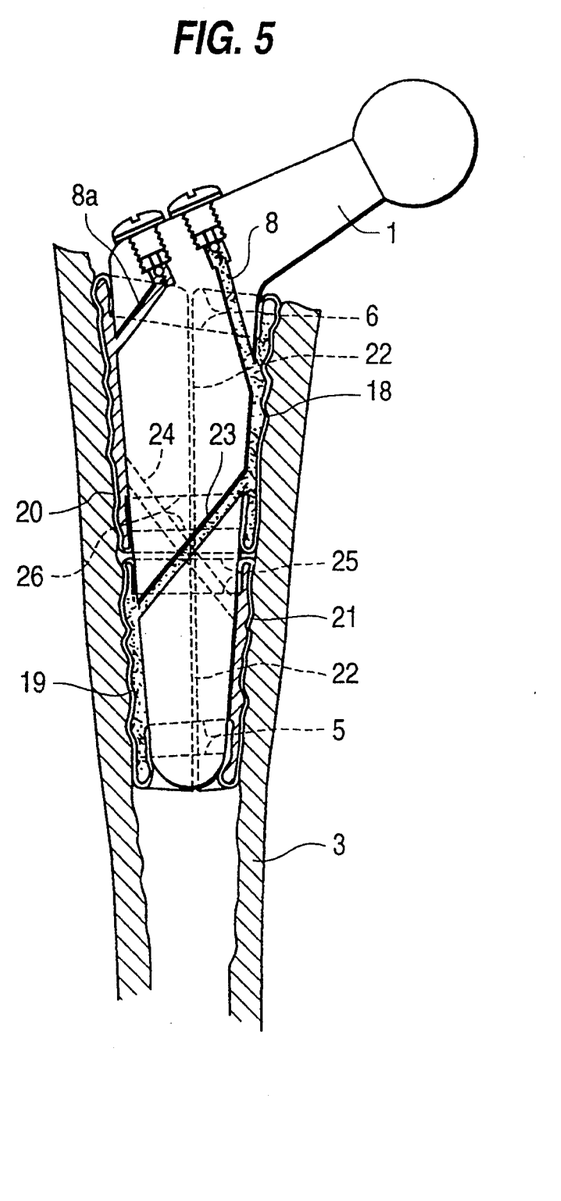
FIG. 5 is a longitudinal section of the invention with four chambers.
Figure 5A:
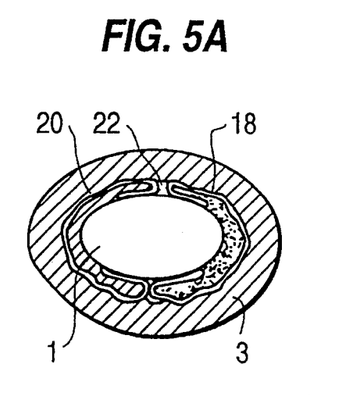
FIG. 5A is a cross-section at the center zone of the stem of FIG. 5.

A further preferred embodiment of the stem is shown in FIGS. 5 and 5A in which the danger that the prosthesis shall rotate is particularly decreased. A total of four chambers 18, 19, 20, 21 is present in this embodiment, with each pair of periprosthetically mounted chambers 18, 19 and 20, 21 being connected to each other in a pressure-tight manner. The four chambers 18, 19, 20, 21 abut along the boundary line 22 in the sagittal plane of the prosthetic stem. Basically, the chambers are affixed to the prosthesis stem in the manner shown by the embodiment of FIG. 1. However, in this embodiment with four chambers, besides the distal and proximal affixing zones 5 and 6, additional central affixing zones 25 and 26 are present along the boundary line 22.

Accordingly, the two proximal-medial and distal-lateral chambers 18 and 19 in practical terms are specifically stressed by the torques and the other two proximal-lateral and distal-medial chambers 20 and 21 by the pure insertion forces. The proximal-medial chamber 18 is connected through a connection duct 23 to the distal-lateral chamber 19. Both chambers 18, 19 may be expanded by means of the filler passing through the injection duct 8. The proximal-lateral chamber 20 communicates through the connection duct 24 with the distal-medial chamber 21. These two chambers 20, 21 may be expanded with filler passing through the injection duct 8A.

Figure 6:
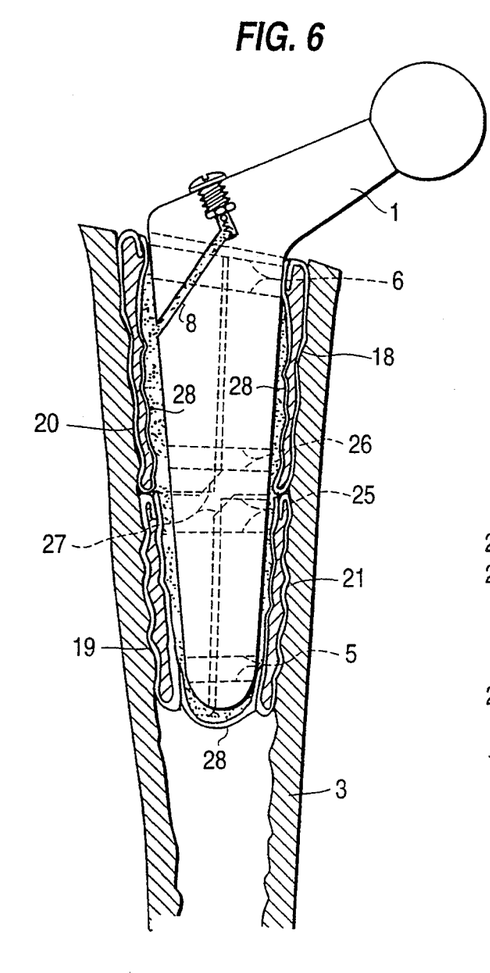
FIG. 6 is a longitudinal section of a stem of FIG. 5 with an additional chamber enclosing the prosthesis stem.

In lieu of the inner connection ducts 23 and 24 shown in FIG. 5, external communication means 27 may also be provided at the surface of the prosthesis, in the manner illustrated in the embodiment of FIG. 6.

A complex form of the multi-chamber principle shown in FIGS. 5 and 6 can be achieved with a prosthesis having a plurality of chambers communicating pairwise through the prosthesis. This communication serves to balance the hydrostatic pressure. The plurality of chambers, depending on the interconnection of the communication ducts, allows centering the prosthesis with a displacement-free interface bone prosthesis.

In the further embodiment mode of the stem of the invention shown in FIG. 6, the stem of FIG. 5 was modified by providing, in addition to the four chambers 18, 19, 20, 21, an inner chamber 28 completely enclosing the stem and separating the four chambers 18, 19, 20, 21 from the prosthesis. Upon insertion of the stem into the marrow cavity, this enclosing chamber 28 can be filled with a heat-resistant cement, whereby an effect similar to that described with reference to FIGS. 3 and 4 can be achieved.

Figure 7:
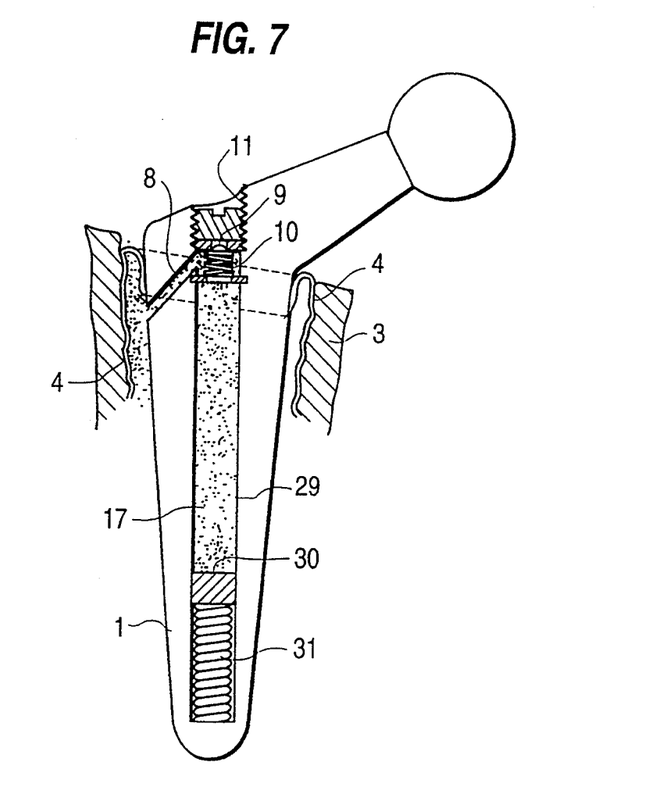
FIG. 7 is a longitudinal section of a stem of the invention with a filler reservoir.
Figure 8:
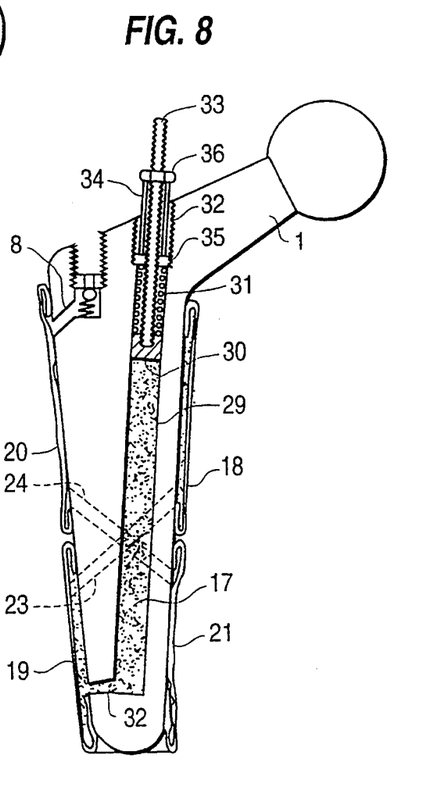
FIG. 8 is a longitudinal section of a stem of the invention with a pre-pressurizable filler reservoir in the unpressurized state.
Figure 9:
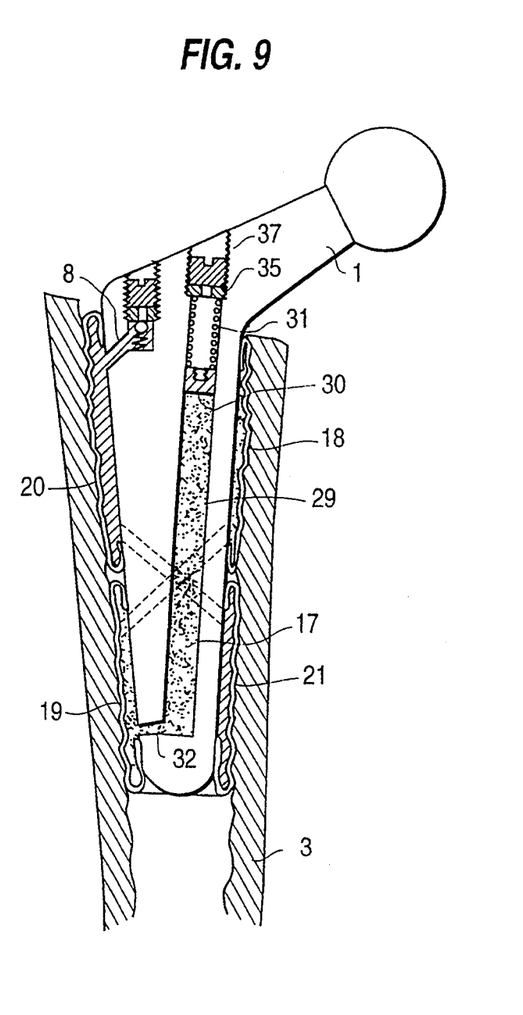
FIG. 9 is a longitudinal section of the stem of FIG. 8 in the stressed state.

Different embodiments of the stem of the invention are shown in FIGS. 7-9, wherein a thermoplastic filler 17 is used.

Figure 7A:
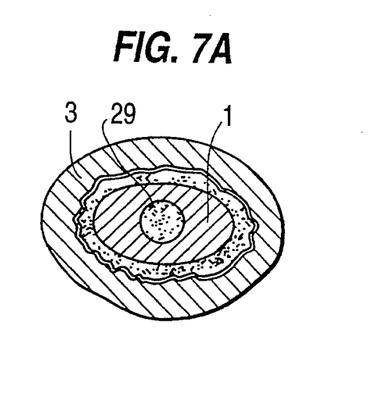
FIG. 7A is a cross-section at the center of the stem of FIG. 7.

The stem shown in FIGS. 7 and 7A comprises an internal reservoir 29 for the thermoplastic 17 which is pressurized by the piston 30 loaded by the spring 31. As a result, the pressure in the chamber 4, which might drop on account of bone transformation (bone resorption), can be maintained. Therefore, as needed, the thermoplastic 17 can be replenished from the reservoir through valve 9 by means of the spring 10 and through the injection duct 8 into the chamber 4.

FIG. 8 shows the "secured" position of the spring 31 during insertion of the prosthesis into the marrow cavity. In this position the thermoplastic material 17 is as yet un-pressurized. If the threaded rod 33, the nut 36 and the prestressing sleeve 34 are then removed, the spring 31 is released and the piston 30 presses against the thermoplastic 17 as shown in FIG. 9. This will take place once the prosthesis has been introduced into its definitive position.

Figure 10:
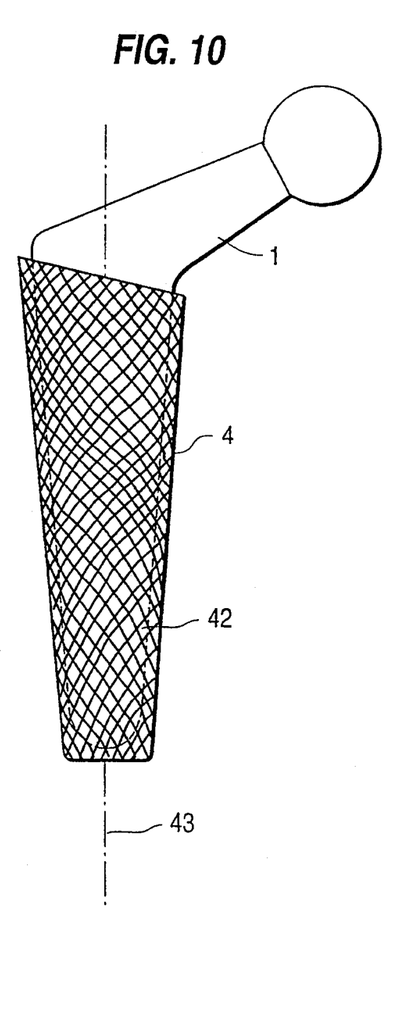
FIG. 10 is a perspective elevation of the stem of the invention of which the chamber consists of a braid.

FIG. 10 shows the outside of the chamber 4 of a prosthesis stem 1 of the invention which includes a braid of two mutually crossing series of fibers 42 with a slant of approximately 45° to the stem axis 43.

Figure 11:
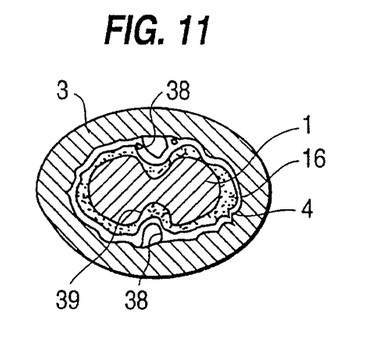
FIG. 11 is a cross-section at the center of the stem of the invention of which the chamber comprises an external rail used for longitudinal vascularization.

FIG. 11 shows a stem of the invention with a simple accessory for the prosthetic chamber 4. This accessory is a U-shaped, for instance one-third tubular rail 38 which can be inserted through the chamber 4 into matching antero-posterior notches 39 in the prosthesis stem 1. These rails 38 face the bone 3 by their openings and allow rapid buildup of medullar vascularity.

We claim:

1. A stem assembly for an endoprosthesis to be anchored in a bone comprising a stem;
    means defining at least one expansible chamber (4) having a first wall sealed to said stem in a pressure-tight manner and a second wall at least partly enclosing said stem (1) and being expandable to contact an interior surface of said bone;
    a viscous liquid filler; and
    valve means for selectively introducing said filler into said chamber for expanding and substantially permanently pressurizing said chamber with hydrostatic pressure.

2. A stem assembly according to claim 1 wherein said filler is a fluid.

3. A stem according to claim 1 or 2 wherein said chamber (4) is periprosthetic.

4. A stem according to claim 1 or 2 wherein said means defining said at least one chamber includes a wall made of silicone.

5. A stem according to claim 1 or 2 wherein said means defining said at least one chamber includes a wall comprising braid impregnated with silicone.

6. A stem according to claim 5, wherein said braid includes two mutually crossing series of fibers (42) evincing a slope of about 45° relative to the stem axis (43).

7. A stem according to claim 6 wherein fibers of said braid are made of a material selected from the group consisting of carbon, polyester and polyamide.

8. A stem according to claim 1 or 2 wherein said means defining said at least one chamber includes a wall having a thickness of less than 0.5 mm.

9. A stem according to claim 1 or 2 wherein said means defining said at least one chamber includes a wall of said chamber (4) having more tensile strength in a proximal region (41) and in a distal region (7) than in a central region.

10. A stem according to claim 1 or 2 wherein said means defining said at least one chamber includes an outside surface coated with hydroxy-apatite particles.

11. A stem according to claim 1 wherein said valve means in said chamber (4) includes a one-way valve (9).

12. A stem according to claim 1 or 2 wherein said means defining said at least one chamber (4) includes means for affixing said at least one chamber to said prosthesis stem (1) such that said stem when implanted is capable of limited axial displacement relative to said bone and said chamber is axially immovable relative to said bone.

13. A stem according to claim 1 or 2 wherein said means defining said at least one chamber (4) includes, at least at the surface facing the bone (3), a biocompatible material.

14. A stem according to claim 1 or 2 wherein said means defining said at least one chamber (4) is formed, at least at the surface facing the bone (3), with a carbonaceous textured surface.

15. A stem according to claim 2 wherein said filler (16) comprises a liquid thickened with filler particles of carbon.

16. A stem assembly according to claim 8 wherein said wall has a thickness of less than 0.25 mm.

17. A stem according to claim 1 or 2 wherein said means defining said at least one chamber includes a wall made of polyurethane.

18. A stem according to claim 1 or 2 wherein said means defining said at least one chamber includes a wall comprising braid impregnated with polyurethane.

19. A stem according to claim 1 or 2 wherein said means defining said at least one chamber includes an outside surface coated with carbon particles.

20. A stem according to claim 1 wherein said chamber is expansible to occupy substantially all space in said cavity between said stem and said bone.

21. A stem according to claim 20 wherein said chamber is collapsed and is tightly against said stem during insertion and is subsequently expanded.

* * * * *